(12) United States Patent
Peterson et al.

(10) Patent No.: US 11,350,981 B2
(45) Date of Patent: Jun. 7, 2022

(54) INDICATION SYSTEM FOR SURGICAL DEVICE

(71) Applicant: Encision Inc., Boulder, CO (US)

(72) Inventors: Shane Peterson, Boulder, CO (US); Michael John Biggs, Denver, CO (US); Philip Schreiber, Boulder, CO (US); Brian Jackman, Salt Lake City, UT (US); David Newton, Longmont, CO (US); Gregory Jude Trudel, Broomfield, CO (US)

(73) Assignee: ENCISION INC., Boulder, CO (US)

( * ) Notice: Subject to any disclaimer, the term of this patent is extended or adjusted under 35 U.S.C. 154(b) by 509 days.

(21) Appl. No.: 15/824,530

(22) Filed: Nov. 28, 2017

(65) Prior Publication Data

US 2018/0147000 A1    May 31, 2018

Related U.S. Application Data

(60) Provisional application No. 62/428,100, filed on Nov. 30, 2016.

(51) Int. Cl.
*A61B 18/12* (2006.01)
*A61B 18/14* (2006.01)
*A61B 18/00* (2006.01)

(52) U.S. Cl.
CPC .......... *A61B 18/1233* (2013.01); *A61B 18/12* (2013.01); *A61B 18/14* (2013.01); *A61B 2018/00702* (2013.01); *A61B 2018/00755* (2013.01); *A61B 2018/00827* (2013.01); *A61B 2018/00875* (2013.01); *A61B 2018/00892* (2013.01)

(58) Field of Classification Search
None
See application file for complete search history.

(56) References Cited

U.S. PATENT DOCUMENTS

| | | | | |
|---|---|---|---|---|
| 3,642,008 A | * | 2/1972 | Bolduc | H01R 11/24 607/152 |
| 5,312,401 A | * | 5/1994 | Newton | A61B 18/14 606/46 |
| 5,897,529 A | * | 4/1999 | Ponzi | A61M 25/0147 604/95.04 |
| 5,936,536 A | * | 8/1999 | Morris | G01R 31/52 340/647 |
| 6,074,382 A | * | 6/2000 | Asah | A61B 18/203 606/10 |
| 8,529,437 B2 | | 9/2013 | Taylor et al. | |
| 9,254,165 B2 | | 2/2016 | Aronow et al. | |

(Continued)

*Primary Examiner* — Ronald Hupczey, Jr.
(74) *Attorney, Agent, or Firm* — Neugeboren O'Dowd PC

(57) ABSTRACT

A cable assembly and methods for indicating an electrical measurement in an electrosurgical instrument are disclosed. The assembly has a circuit having a voltage sensor, a current sensor, and a processing device operatively coupled to the at least one active conductor. The assembly also has a substantially electrically non-conductive housing enclosing the circuit and a portion of at least one active conductor, and exposing a contact portion of the at least one active conductor, the at least one active conductor configured to conduct power to an electrosurgical instrument. The assembly also has an indicator operatively coupled to the processing device.

13 Claims, 6 Drawing Sheets

(56) References Cited

U.S. PATENT DOCUMENTS

| | | | |
|---|---|---|---|
| 2012/0283718 A1* | 11/2012 | Cosmescu | A61B 18/1402 606/33 |
| 2013/0317496 A1 | 11/2013 | Newton et al. | |
| 2016/0106494 A1 | 4/2016 | Aronow et al. | |
| 2016/0192980 A1 | 7/2016 | Newton et al. | |

* cited by examiner

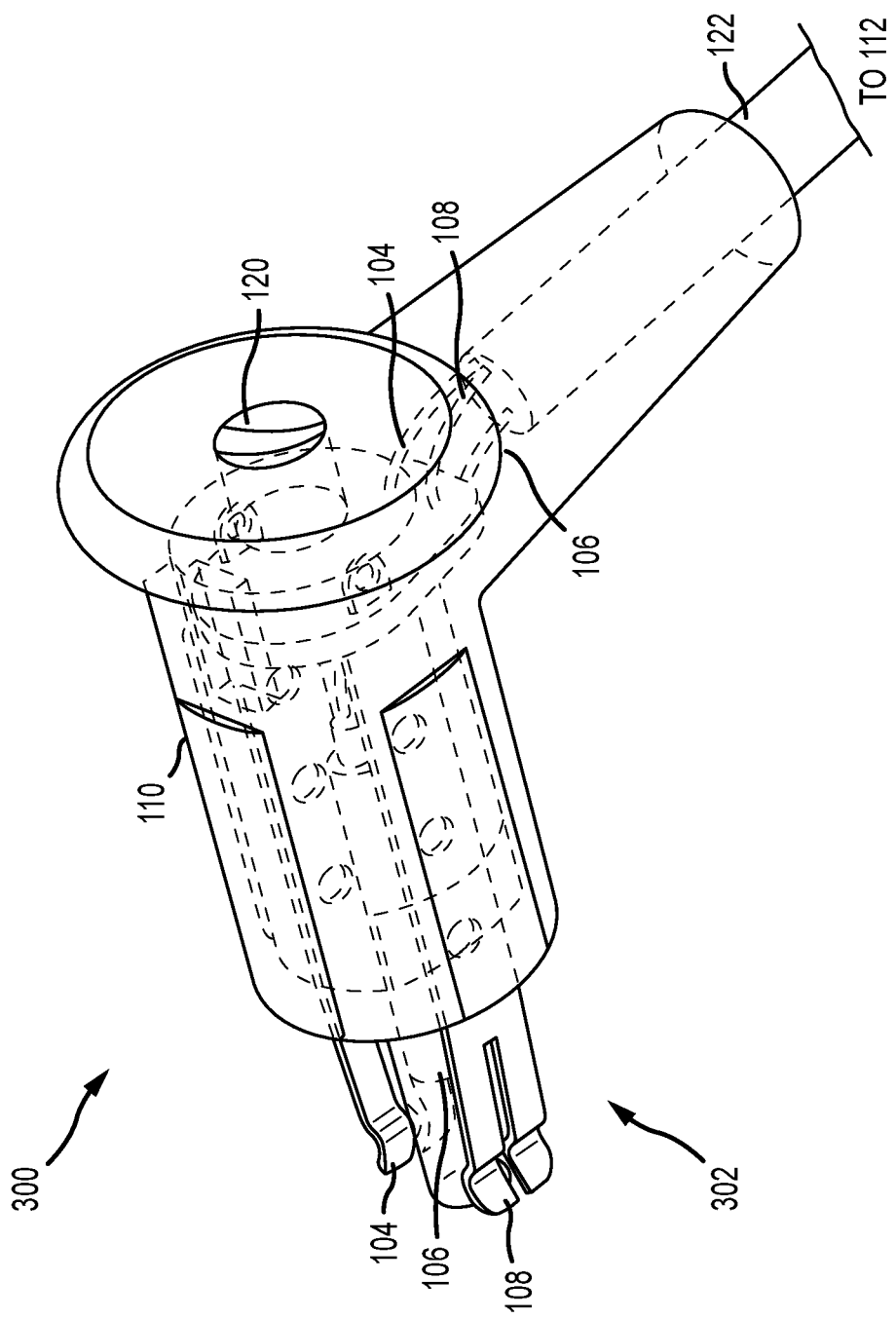

INDICATION SYSTEM FOR SURGICAL DEVICE

CLAIM OF PRIORITY UNDER 35 U.S.C. § 119

The present application for patent claims priority to U.S. Provisional Patent Application No. 62/428,100, filed Nov. 30, 2016, and assigned to the assignee hereof, the contents of which are hereby expressly incorporated by reference herein.

FIELD OF THE INVENTION

The present invention relates to a surgical device. In particular, but not by way of limitation, the present invention relates to systems and methods for indicating electrical activity in a surgical device.

BACKGROUND

U.S. Patent Publication 2013/0317496 A1 to Newton et al., and published on Nov. 28, 2013, discloses an enhanced control system for electrosurgical applications, the contents of which are incorporated herein by reference for all proper purposes.

U.S. Pat. No. 8,529,437 to Taylor et al., and published on Sep. 10, 2013, discloses a multifunctional surgical instrument, the contents of which are incorporated herein by reference for all proper purposes.

U.S. Pat. No. 9,254,165 to Aronow et al., and published on Feb. 9, 2016, discloses a system and method for detecting faults in an electrosurgical instrument, the contents of which are incorporated herein by reference for all proper purposes.

Although the present devices and methods are functional, a system and method are needed to improve the present technology, and/or to provide other new and innovative features.

SUMMARY

An exemplary cable system for indicating an electrical measurement in an electrosurgical instrument has a circuit having at least one of a voltage sensor, or current sensor, and a processing device operatively coupled to the at least one active conductor. The exemplary system also has a substantially electrically non-conductive housing enclosing the circuit and a portion of at least one active conductor, and exposing a contact portion of the at least one active conductor, the at least one active conductor configured to conduct power to an electrosurgical instrument. The exemplary system also has an indicator operatively coupled to the processing device.

An exemplary method of making a cable assembly for indicating an electrical measurement in an electrosurgical instrument includes providing a substantially electrically non-conductive housing. The exemplary method also includes enclosing a portion of at least one active conductor and exposing a contact portion of the at least one active conductor with the non-conductive housing, the at least one active conductor configured to conduct power to an electrosurgical instrument. The exemplary method also includes enclosing a circuit having a voltage sensor, a current sensor, and a processing device operatively coupled to the at least one active conductor with the non-conductive housing. The exemplary method also includes operatively coupling an indicator to the processing device.

BRIEF DESCRIPTION OF THE DRAWINGS

FIG. 3 illustrates a partially-transparent view of the indication system;

DETAILED DESCRIPTION

Figure 1:
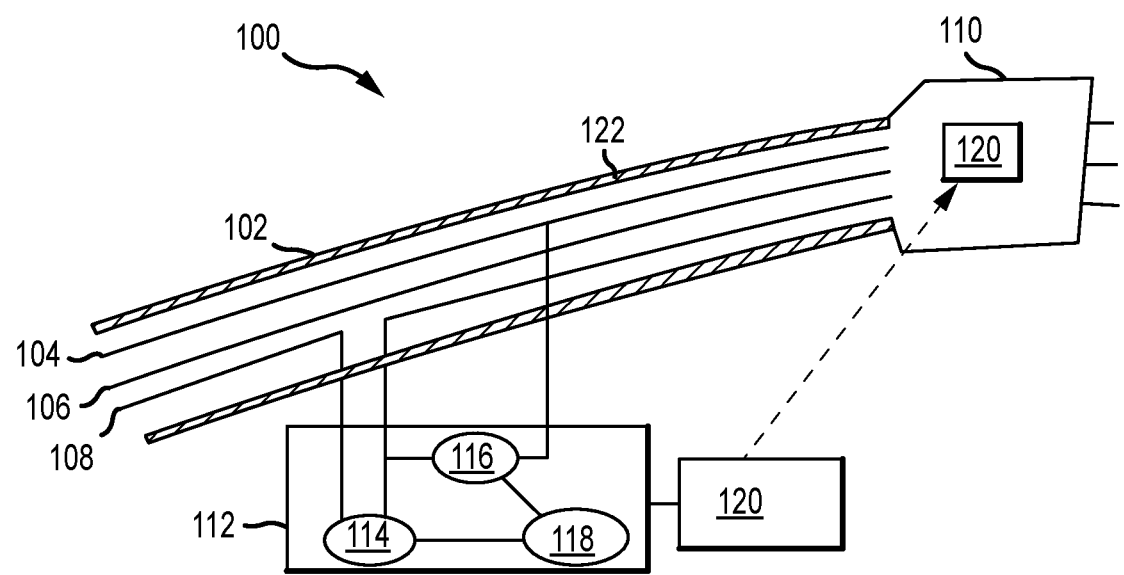
FIG. 1 illustrates a schematic view of an indication system.

Exemplary embodiments of a cable system are shown in the drawings and summarized below. A system and method for providing an indication of an electrical measurement, wherein the system is contained substantially within a cable, is provided in some embodiments. The measurement may be a magnitude of an electrosurgical current, voltage, or power in the conductors of a cable. An associated method may include processing signals transmitted by the cable. In some embodiments, an electrosurgical current may be a shield current conducted through the cable from a minimally invasive surgical instrument or a voltage between two conductors.

A system or method may simultaneously have features described in US Pat. Pub. No. 2016/0192980 A1, published Jul. 7, 2016, entitled Enhanced Control Systems Including Flexible Shielding and Support Systems for Electrosurgical Applications, the entirety of which is incorporated herein by reference and/or any one of the features described in US Pat. Pub. No. 2016/0106494 A1, published Apr. 21, 2016, entitled Multiple Parameter Fault Detection in Electrosurgical Instrument Shields, the entirety of which is incorporated herein by reference.

In some embodiments, an indication system for providing indications of any electrical measurement or activity is provided. Specifically, the system may be provided to detect and indicate that a voltage and/or a current measurement has been detected, such as in a medical instrument. In some embodiments, the system may be contained substantially within a cable. The measurement may be the magnitude of electrosurgical current, voltage, impedance or power in the conductors of a cable. The system may also involve processing of signals transmitted by the cable. Specifically, the measurement may be electrosurgical shield current conducted through the cable from a shielded minimally invasive instrument.

Referring now to the drawings, where like or similar elements are designated with identical reference numerals throughout the several views, and referring in particular to FIG. 1, it illustrates a block diagram of an indication system 100 according to some embodiments. The system may include a cable having sensors and electronics to make measurements and provide display of any electrical parameter; for example, voltage, current, power, impedance from any source, such as an electrosurgical instrument. The system 100 may have a flexible cable 102 comprising a plurality of active conductors 104, 106, 108 and a plug 110 configured to couple to an electrosurgical instrument (not illustrated). The system 100 may also have a circuit 112 having a current sensor 114, a voltage sensor 116, and a processing device 118. The circuit 112 may be configured to control a display 120, at least a portion of which may be located external to the cable 102 and/or on or at the plug 110. A non-conductive housing 122 may be provided about portions of the system 100. The system 100 may include many types of electrical cables or may be specific only to shield currents from laparoscopic instruments.

Figure 2:
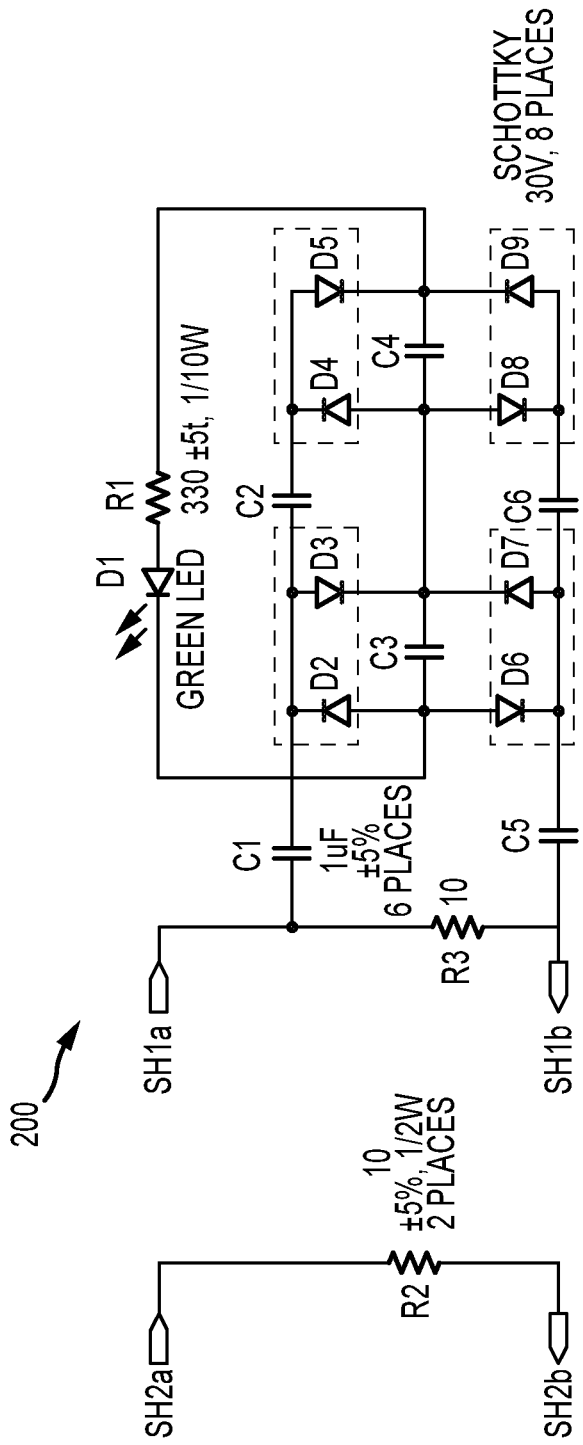
FIG. 2 illustrates a schematic view of circuitry suitable for use in the indication system in FIG. 1.

FIG. 2 illustrates details of a circuit 200 suitable for use in the system 100 previously described herein. As one skilled in the art can appreciate from reviewing FIG. 2, in some embodiments, the circuit 200 may be configured to cause the display 120 to illuminate when the system 100 is in a defined state of operation.

Figure 2A:
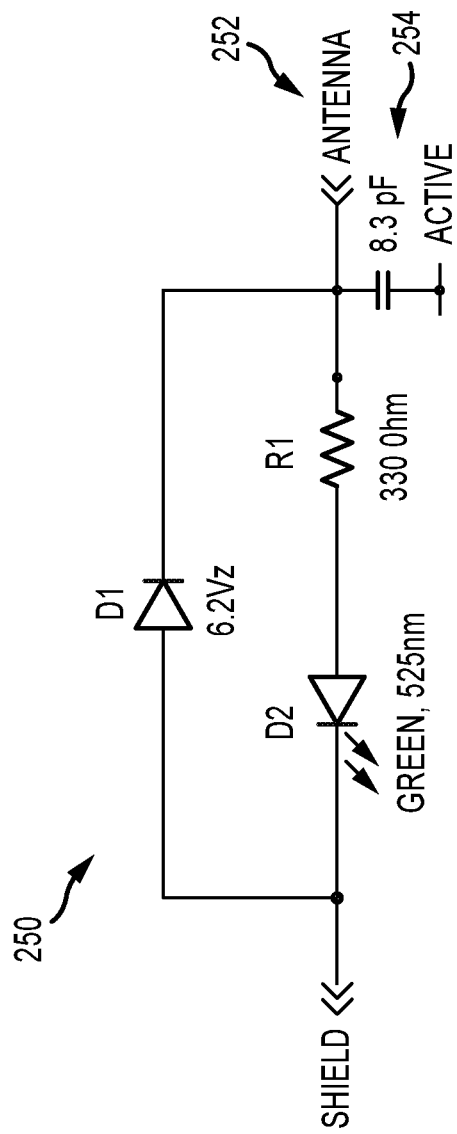
FIG. 2A illustrates a schematic view of circuitry suitable for use in the indication system in FIG. 1.

FIG. 2A illustrates details of a circuit 250 suitable for use in the system 100 previously described herein. As illustrated, the circuit 250 may include an antenna 252 or a capacitor 254. In some embodiments, the capacitor may be an 8.3 picofarad (pF) capacitor 254. In some embodiments, the antenna serves as the capacitor 254. In some embodiments, the capacitor 254 is a discrete feature of the circuite 250.

Turning now to FIG. 3, in some embodiments, the system 300 may include a connector assembly 302 configured to couple to a shielded electrosurgical instrument (not illustrated). For example, the cable 102 may have three conductors 104, 106, 108 configured as shield contacts 104, 108 and an active electrode contact 106 respectively, and a plug 110 shaped and configured to couple to a shielded electrosurgical instrument.

As seen in the system 300 illustrated in FIG. 3, the display 120 may be an LED and an ABS light pipe configured to shine solid green, for example, with a dominant wavelength of 525 nM when the system 300 senses protective conditions in the shielded electrosurgical instrument.

In some embodiments, the system 100 is configured to cause the display 120 to flash a set number of times when the shielded electrosurgical instrument is first powered on and a fault current is not detected. In some embodiments, the system 100 is configured to cause the display 120 to illuminate or to change colors of illumination such from amber to green when the electrosurgical instrument is in a suitable state for safe operation.

Figure 4:
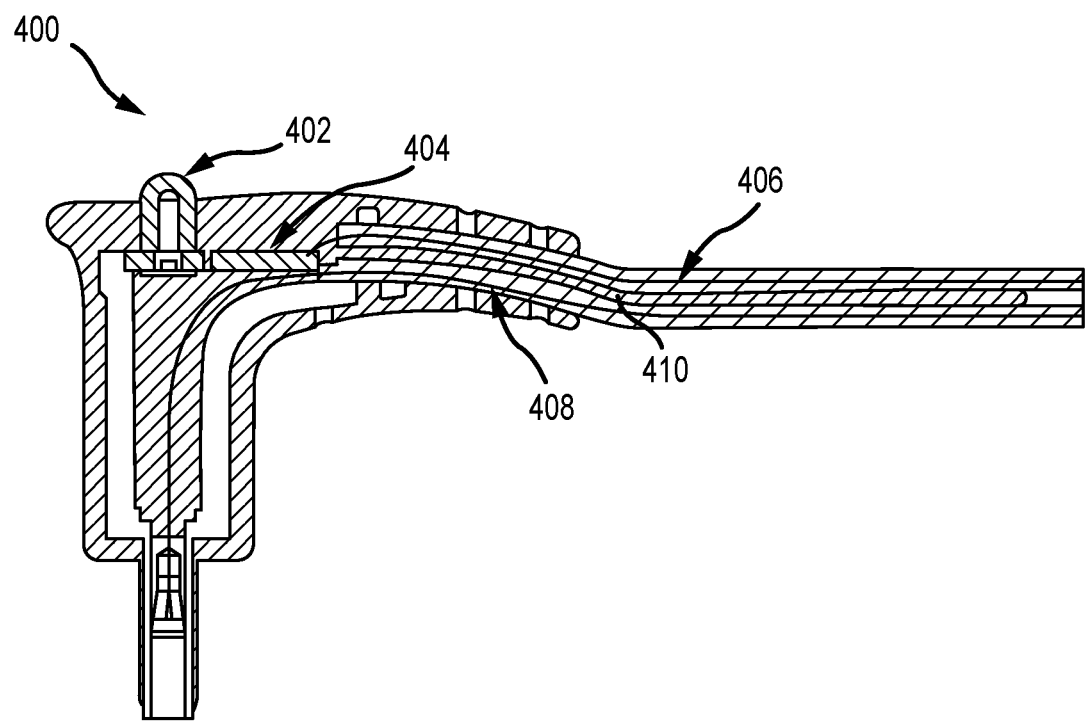
FIG. 4 illustrates a side section view of the indication system.

FIG. 4 illustrates a system having an antenna. That is, the system 400 may include an indicator 402 substantially as previously described herein and a circuit board 404 having a circuit 200, 250 such as the circuit described with reference to FIG. 2 or 2A. The system 400 may also have one or more shield conductors 406 as previously described herein and/or as described in one of the documents incorporated herein by reference. The system 400 may also have one or more active conductors 408 as previously described herein and/or as described in one of the documents incorporated herein by reference. The system 400 may also have an antenna or antenna wire 410, such as that illustrated in FIG. 4. In some embodiments, the antenna or antenna wire 410 may be provided to detect capacitive energy and to create a current in the sensor. The antenna 410 may be a length of wire, such as about 12 inches or less, or between about 3 and 9 inches, or about 6 inches, projecting into a lumen formed in a center of the cable. The antenna wire 410 may be positioned in sufficiently close proximity to the active conductor 408 so as to cause a capacitive effect. In some embodiments, capacitor 254 illustrated in FIG. 2A may be provided by the antenna 410 and the active conductor 408.

In some embodiments, the system 100 may be limited to electrosurgical parameters, for example current in a bipolar applications or power in either bipolar or monopolar applications.

In some embodiments, the system 100 may be limited to shielded monopolar applications in which the parameter of interest is shield current, or applied active voltage.

In some embodiments, the system 100 may be powered, by one or more sources such as by a portion of power conducted within the cable, by a battery in the cable, or by an external power source, for example a source within connected equipment.

In some embodiments, a display providing indications may be a single LED, multiple LEDs, one or more LCD elements, a segmented or dot-matrix display, or other appropriate display technology.

The display may be located on a component of the cable. The component may be the plug—head that connects a laparoscopic instrument to a high-frequency energy source. The high-frequency energy source may include a monitor for control of the energy in response to the properties of the shield current conducted from a shielded instrument.

The measurement and display processing circuitry may be located within a component of the cable.

Figure 5:
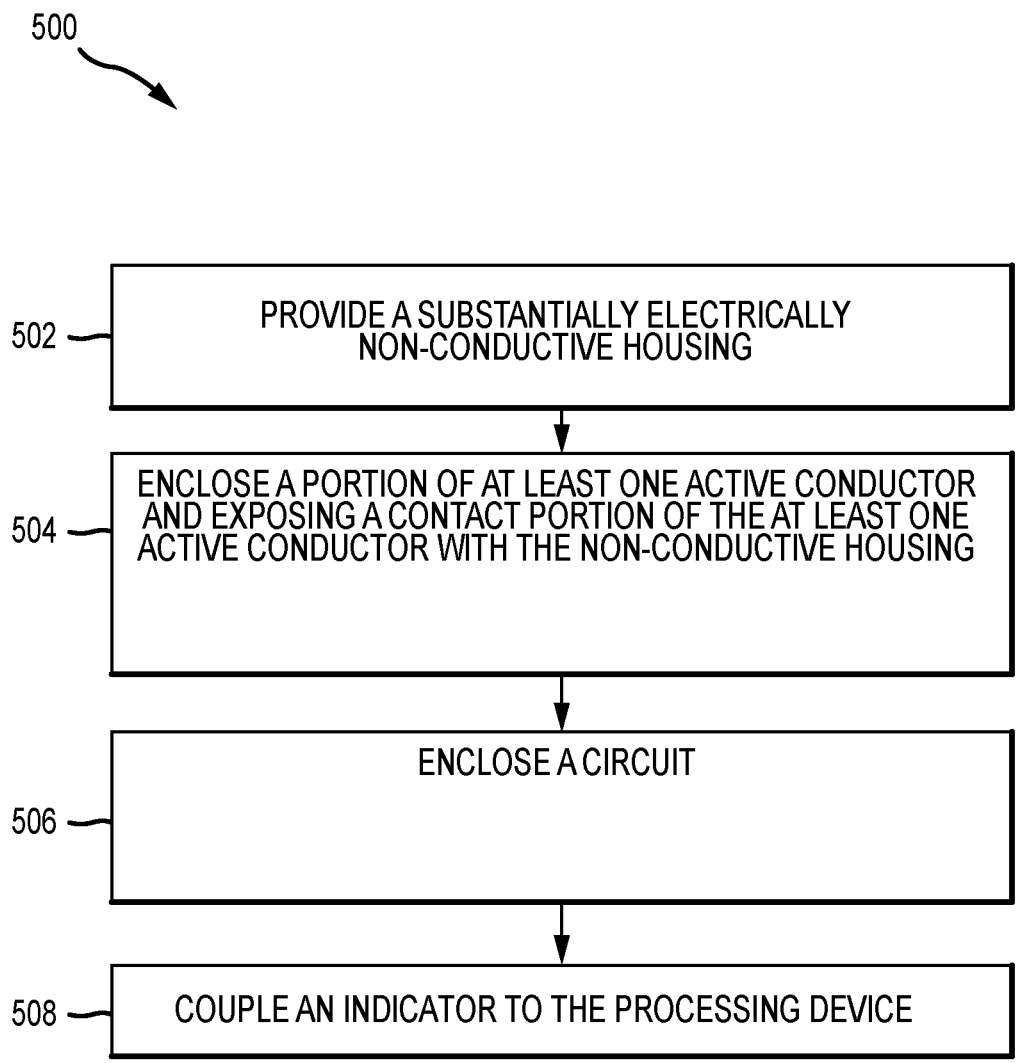
FIG. 5 is a flowchart of a method.

Turning now to FIG. 5, a method 500 of making a cable assembly is described. The method 500 may include providing 502 a substantially electrically non-conductive housing; and enclosing 504 a portion of at least one active conductor and exposing a contact portion of the at least one active conductor with the non-conductive housing, the at least one active conductor configured to conduct power to an electrosurgical instrument. The method 500 may include enclosing 506 a circuit having a voltage sensor, a current sensor, and a processing device operatively coupled to the at least one active conductor with the non-conductive housing; and operatively coupling 508 an indicator to the processing device.

The method may include enclosing a shield current conductor with the non-conductive housing; and operatively coupling the voltage sensor, the current sensor, and the processing device to the at least one shield current conductor.

The method may include configuring the system to be powered by a portion of power diverted from the at least one active conductor.

The method may include positioning an antenna in sufficiently close proximity to the at least one active conductor so as to cause a capacitive effect; and operatively coupling the antenna to the circuit; and configuring at least one of the current sensor are the voltage sensor to detect capacitive energy.

Embodiments of the invention can be embodied in a variety of ways. In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of an "LED" should be understood to encompass disclosure of the act of "lighting"—whether explicitly discussed or not—and, conversely, were there only disclosure of the act of "lighting", such a disclosure should be understood to encompass disclosure of a "lighting mechanism". Such changes and alternative terms are to be understood to be explicitly included in the description.

Moreover, the claims shall be construed such that a claim that recites "A, B, and/or C" shall read on a device that requires "A" only; similarly, the claim shall read on a device that requires "A+B". A claim that recites "at least one of A, B, or C" shall read on a device that requires "A" only.

The claims shall be construed such that any relational language (e.g. perpendicular, straight, etc.) is understood to mean within a reasonable manufacturing tolerance at the time the device is manufactured or at the time of the invention, whichever is greater.

In conclusion, the present invention provides, among other things, a system and method for indication of an electrical measurement, wherein the system is contained substantially within a cable. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A cable system for indicating an electrical measurement in an electrosurgical instrument, the system comprising:
    a circuit having a processing device operatively coupled to at least one active conductor, and at least one of a voltage sensor or a current sensor;
    an antenna operatively coupled to the circuit, wherein the antenna is positioned adjacent to the at least one active conductor so as to cause a capacitive effect;
    a substantially electrically non-conductive housing enclosing the circuit, at least one shield current conductor, and a portion of the at least one active conductor, wherein the non-conductive housing exposes a contact portion of the at least one active conductor, the at least one active conductor configured to conduct power to an electrosurgical instrument, and wherein the at least one shield current conductor is configured to conduct shield current from the electrosurgical instrument, and wherein at least one of the voltage sensor or the current sensor, and the processing device are operatively coupled to the shield current conductor; and
    an indicator operatively coupled to the processing device.

2. The system according to claim 1, wherein:
    the system is configured to indicate a current in a bipolar electrosurgical application in response to receiving a signal from the current sensor and determining the signal has a nonzero value.

3. The system according to claim 1, wherein:
    the system is configured to indicate a current in a monopolar electrosurgical application.

4. The system according to claim 1, wherein:
    the system is configured to indicate the shield current in a shielded monopolar electrosurgical application in response to receiving a signal from the current sensor and determining the signal has a nonzero value.

5. The system according to claim 1, wherein:
    the indicator comprises one of the group consisting of a single LED, a plurality of LEDs, a single LCD element, a plurality of LCD elements, a segmented display, and a dot-matrix display.

6. The system according to claim 1, wherein:
    the system is powered by a portion of power diverted from the at least one active conductor.

7. The system according to claim 1, further comprising:
    a capacitor, wherein the capacitor is provided by the antenna and the at least one active conductor; and wherein
    the voltage sensor is configured to detect capacitive energy.

8. The cable system according to claim 1, wherein the at least one shield current conductor comprises a first shield current conductor and a second shield conductor, and wherein the at least one active conductor is positioned between the first shield current conductor and the second shield current conductor.

9. The cable system according to claim 8, wherein the electrosurgical instrument is a shielded electrosurgical instrument, and wherein the cable system further comprises:
    a plug shaped and configured to couple the shielded electrosurgical instrument to a high-frequency energy source, wherein the high-frequency energy source includes a monitor for control of the power in response to properties of the shield current conducted from the shielded electrosurgical instrument.

10. A method of making a cable assembly for indicating an electrical measurement in an electrosurgical instrument, the method comprising:
    providing a substantially electrically non-conductive housing;
    enclosing at least one shield current conductor within the non-conductive housing, wherein the at least one shield current conductor is configured to conduct shield current from the electrosurgical instrument;
    enclosing a portion of at least one active conductor and exposing a contact portion of the at least one active conductor within the non-conductive housing, wherein the at least one active conductor is configured to conduct power to an electrosurgical instrument;
    enclosing a circuit having a processing device operatively coupled to the at least one active conductor within the non-conductive housing, and at least one of a voltage sensor or a current sensor;
    operatively coupling at least one of the voltage sensor or the current sensor, and the processing device to the at least one shield current conductor;
    operatively coupling an antenna to the circuit, wherein the antenna is positioned adjacent to the at least one active conductor so as to cause a capacitive effect; and
    operatively coupling an indicator to the processing device.

11. The method according to claim 10, wherein:
    the indicator comprises one of the group consisting of a single LED, a plurality of LEDs, a single LCD element, a plurality of LCD elements, a segmented display, and a dot-matrix display.

12. The method according to claim 10, further comprising:
    configuring the system to be powered by a portion of power diverted from the at least one active conductor.

13. The method according to claim 10, further comprising:
    providing a capacitor, wherein the capacitor is provided by the antenna and the at least one active conductor; and
    configuring the voltage sensor to detect capacitive energy.

* * * * *